United States Patent [19]

Cooper

[11] Plant 4,741

[45] Jun. 16, 1981

[54] GRANNY SMITH APPLE TREE (GREENSPUR STRAIN)

[75] Inventor: Calvin L. Cooper, Brewster, Wash.

[73] Assignee: Auvil Fruit Co., Inc., Orondo, Wash. ; a part interest

[21] Appl. No.: 141,310

[22] Filed: Apr. 18, 1980

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Eugene D. Farley

[57] ABSTRACT

The presently described apple tree originated as a generic bud sport on a Hannaford Spur Granny Smith apple tree (U.S. Plant Pat. No. 3,453) in the Calvin L. Cooper orchard located in Brewster, Wash. The new apple tree and its fruit are characterized by the desirable properties which characterize the parent Hannaford Granny Smith. In addition, it is characterized by significantly increased bloom set, by significantly higher setting of double and triple apple clusters, by sharply increased productivity, and by materially reduced internodal distances on the terminal growth of its branches.

4 Drawing Figures

DESCRIPTION

The present invention relates to a new and distinct variety of apple tree which was discovered by me as a genetic bud sport on a Hannaford Spur Granny Smith apple tree (U.S. Plant Pat. No. 3,453 in my cultivated orchard in the State of Washington in Brewster, Wash.

In May of 1969 I top-worked several Hannaford Granny Smith apple trees in my orchard aforesaid. I top-worked them to the only known spur-type Granny Smith apple tree, the Hannaford Granny Smith.

As time went on I observed that a particular branch of one of these trees bloomed especially well. In the year 1972 it fruited particularly heavily. It fruited consistently heavily in succeeding years. I also observed that this particular branch set a much greater number of double and triple apple clusters in comparison to the parent Hannaford Granny Smith strain. In contrast, the branches of the other trees that were top-worked to Hannaford Granny Smith produced a light crop in 1972 and consistently had relatively low yields from 1972 through 1979. This was true even though the parent strain Hannaford Granny Smith trees had an exceptional number of pollenizer trees of Red Delicious in close proximity each year.

I top-worked grafting with wood of the aforementioned high producing limb selection on a two year old summer apple tree in my Brewster, Wash. orchard. This tree bloomed profusely and fruited heavily in October of 1975. This second generation tree has produced consistently heavy crops from 1975 through 1979. During these same years the productivity of the parent Hannaford Granny Smith was erratic.

In August of 1976 I propagated bud wood from the second generation tree onto approximately 50 large summer apple trees. These trees produced third generation fruits. In this manner, I now have propagated bud wood for a total of 8 generations and have found the outstanding characteristics of my new variety to be permanent and stable. In all generations, as compared with the parent Hannaford Granny Smith apple trees, there was increased bloom set, significantly higher setting of double and triple apple clusters and sharply increased productivity.

The accompanying drawings illustrate my new apple tree and the characteristics of its fruit.

FIG. 1 is a photograph of a limb of the tree in full bloom, illustrating the high density of blooms;

FIG. 2 is a photograph of a limb of my new apple tree in its fruit bearing condition, illustrating the high degree of fruit setting;

FIG. 3 is a photograph of an entire tree in its fruit bearing condition, illustrating its semi-dwarf size and its productivity;

Figure 4:
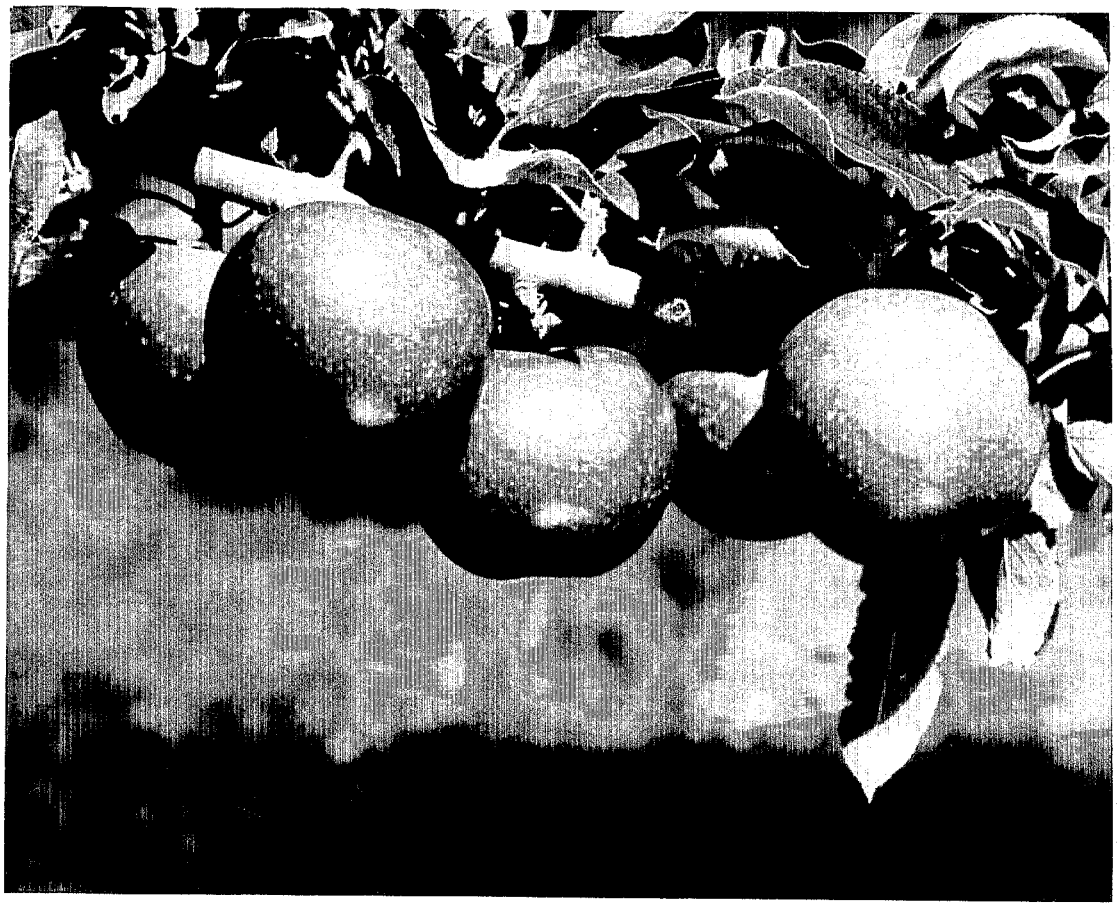
FIG. 4 is a photograph of the fruit borne by my new apple tree.

In general, the tree, leaves and fruit of my new Greenspur Granny Smith apple tree are characterized by many of the features which distinguish the parent Hannaford Granny Smith apple tree from the grandparent standard Granny Smith apple tree.

Thus the tree is spur-type, medium small and semi-dwarf, being between 65% and 75% of the size of the grandparent Granny Smith apple tree. Its growth is vigorous and its form compact. However, the average internodal distances on the terminal growths of its branches are substantially, shorter than are the corresponding dimensions of its ancestors.

I have made internodal distance comparisons on 20 terminals of my new Greenspur Granny Smith and compared them with the similar distances for both the parent Hannaford Granny Smith and the grandparent standard Granny Smith. The values I found were 0.3 inch, 0.5 inch and 0.7 inch, respectively. This characteristic has an obvious relationship to the bearing characteristics of the trees.

With respect to the flowers and leaves, the flowers in general are similar to those of the parent Hannaford strain. However, as illustrated in FIG. 1, they are characterized by a unique high-density of blooms, for Granny Smith type apples.

The leaves also are similar, being deep green in color and dense in contrast with those of the standard Granny Smith grandparent. They have measureably more chlorophyll. Also, they are somewhat larger and more flat than the Hannaford Granny Smith parent.

The fruit is large, dark green and characterized by the presence of numerous and distinctive white spots, as illustrated in the drawings. In the orchards of Northwestern Washington only, the fruit has a pinkish blush, due possibly to a local soil or climate condition.

The fruit is characterized by outstanding marketing properties, in that it has an attractive appearance, is firm with whiter flesh than the parent Hannaford strain and has outstanding storage capabilities. Under controlled atmosphere storage it is possible to store the fruit for a full year while still retaining acceptable marketing qualities.

The principal unique quality of the herein described Greenspur Granny Smith apple tree is its bearing habit.

As noted above, my new apple tree is characterized by significantly increased bloom set, by significantly higher setting of double and triple apple clusters, and by sharply increased productivity, this having been a deficiency of its parent which adversely affected its market acceptance.

To demonstrate the superior productivity of my new Greenspur Granny Smith strain, I studied the development of a large number of its blooms and compared their setting characteristics with the setting characteristics of an equal number of blooms of the parent Hannaford strain Granny Smith apple tree.

In each case 995 individual blooms were considered from 199 blossom clusters of 5 individual blooms. In the case of the parent Hannaford strain Granny Smith apple tree, the pollenizing conditions were superior, since these trees were surrounded by permanent pollenizing Red Delicious apple trees, whereas my new Greenspur strain Granny Smith apple trees were not so located and had only bouquets and puff gun application of Red Delicious pollen.

The results of my study were as follows:

| PARENT HANNAFORD STRAIN | GREENSPUR STRAIN |
|---|---|
| 995 blooms | 995 blooms |
| 199 bloom clusters | 199 bloom clusters |
| 86 apples set | 126 apples set |
| 16 clusters of doubles and triples | 26 clusters of doubles and triples |
| 43 percent apples set in relation to total clusters | 63 percent apples set in relation to total clusters |
| 8 percent clusters in relation to total clusters | 13 percent clusters in relation to total clusters |

The above data conclusively show a significantly higher set in favor of my new Greenspur strain. The relative percent apple set values of 63% vs. 43% indicates a 47% higher setting average for my new Greenspur strain over the parent Hannaford strain. In cluster percentage, my new Greenspur variety shows comparative values of 26 clusters vs. 16 clusters, or a 62% increase in favor of the new Greenspur strain.

A more detailed botanical description of my new apple tree follows. In this description, the color values recited are in accordance with the Nickerson Color Fan published by the American Horticultural Council, Arnold Arboretum, Jamaica Plains, Mass.

Parentage: Sport of 'Hannaford Spur Granny Smith'.

Date of fruit maturity: Matures 5 days later than regular 'Granny Smith'.

*In the Orondo, Wash. area.*—October 15 on M 26 to October 19 on M 7A.

Tree: Compact spur-type tree; Small, vigorous, upright, heavily spurred, annual bearer, heavy production.

*Trunk.*—Thick, straight, smooth bark, light olive-brown (2.5Y 5/5).

*Branches.*—Thick, heavily spurred, short internodes, upright.

*Leaves.*—Medium to large, ovate, point tapered, margin slightly serate; length, $3\frac{1}{2}$ inches, width $2\frac{1}{8}$ inches; thick, color—dark green (5G 4/7); petiole—medium, thick, pubescent. Larger and flatter than Hannaford spur Granny Smith with less tendency to curl.

Flowers:

*Date of first bloom.*—April 25.

*Date of full bloom.*—April 28.

*Color.*—Petals white to very pale purple (7.5 P 9/2) stigma and stile light green (5GY 8/8).

Fruit:

*Maturity when described.*—Mature from mid-season storage.

*Size.*—Medium to large, equatorial diameter 3 inches to $3\frac{3}{4}$ inches.

*Form.*—Uniform, rounded to oblate.

*Cavity.*—Smooth, deep, conical, symmetrical; depth $\frac{5}{8}$ to $\frac{7}{8}$ inches; breadth, $1\frac{1}{4}$ to $1\frac{1}{2}$ inches.

*Stem.*—Medium to light, flexible, well attached.

*Basin.*—Smooth, calyx lobes absent (not glabrous as in 'Delicious'; depth $\frac{1}{2}$ to $\frac{5}{8}$ inches; breadth, $1\frac{1}{2}$ inches.

*Calyx.*—Closed, sepals pointed, prominent in broad basin; sepals pubescent.

*Skin.*—Smooth, glossy, medium thick. Dots—small, white, inconspicuous. Distribution relatively few on fruit shoulders, more numerous toward basin. Color: uniform strong yellowish-green (2.5G 5/9). Darker green in color than standard Granny Smith.

*Flesh.*—White, juicy, crisp. Cut surfaces non-browning. Flavor mild. Quality good.

*Core.*—Core line prominent in cross section, medium size, ovate seed cavities, vascular bundles evenly spaced and inconspicuous; calyx tube closed, narrow, inconspicuous, long; styles persistent, united.

*Stamens.*—In single whorl, persistent.

Seeds: Seed number 4 to 6 at maturity, occasionally more than 1 per cell; length 9/32 to 5/16; breadth, 3/16 inch. Form acute, color reddish brown to chestnut (mixed 10 YR 5/6, 10 YR 4/4).

Use: Dessert, baking, processing.

Keeping quality: Very good; 160 days in cold storage; shelf life very good.

Unique physical characteristics of plant: Parent strain has extremely low fruit set percentage; this strain sets fruit significantly better than parent under same conditions.

I claim:

1. A new and distinct variety of Granny Smith apple tree similar to the parent Hannaford strain Granny Smith apple tree, but characterized by significantly increased bloom set, by significantly higher setting of double and triple apple clusters, by sharply increased productivity, and by materially reduced internodal distances on the terminal growths of its branches.

* * * * *

FIG. 1
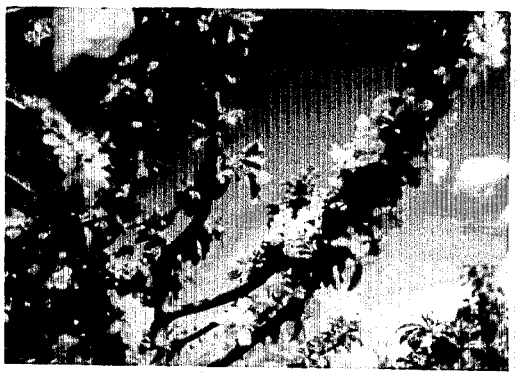
FIG. 2
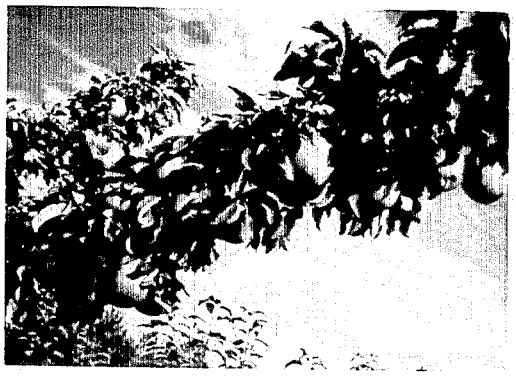
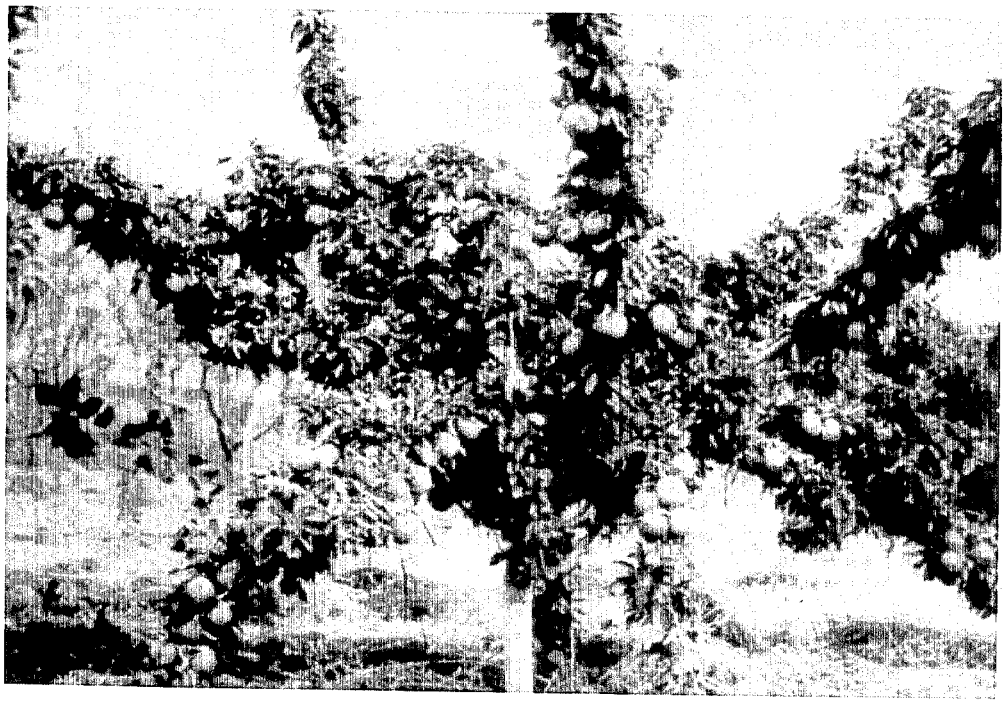
FIG. 3